United States Patent [19]

Pickett et al.

[11] 3,999,625
[45] Dec. 28, 1976

[54] DEVICE FOR SIMULTANEOUS MODULATION AND AMPLIFICATION OF LOW FREQUENCY SOUNDS

[75] Inventors: Charles G. Pickett; Ronald S. Pickett, both of Fort Lee, N.J.

[73] Assignee: L. P. S. Incorporated, Jersey City, N.J.

[22] Filed: Oct. 15, 1975

[21] Appl. No.: 622,458

[52] U.S. Cl. .......................... 181/131; 128/2.05 S; 137/828
[51] Int. Cl.[2] ........................................... A61B 7/02
[58] Field of Search ...................... 128/2 K, 2.05 S; 137/828, 841, 842; 181/129–135

[56] References Cited
UNITED STATES PATENTS

| | | | |
|---|---|---|---|
| 3,398,758 | 8/1968 | Unfried | 137/828 X |
| 3,621,845 | 11/1971 | Oates | 181/131 X |
| 3,690,404 | 9/1972 | Collins | 181/131 |
| 3,693,611 | 9/1972 | Ploss | 181/129 X |

*Primary Examiner*—Lawrence R. Franklin

[57] ABSTRACT

A device for simultaneously modulating and amplifying low frequency sounds which comprises a tubular member having an axial bore extending a distance interiorly of the inlet end thereof and tapering to a reduced axial bore in said tubular member. A generally perpendicular passageway in said tubular member intersects said reduced axial bore, the top wall of which terminates adjacent to said intersection and the bottom wall of which extends past said intersection, said extended portion being deflected a finite angle relative to the normal axial flow. The tubular member is received by a sleeve, and a first baffle flared in the direction of the flow is angularly disposed relative to said sleeve to define a first passageway in said tubular member. A second baffle in spaced relation to the first baffle is also angularly disposed relative to the first baffle, and is also angularly disposed relative to the sleeve, to define a second passageway in said tubular member such that the area of the second passageway is greater than the area of the first passageway. A receptor tube is provided at the outlet end of said tubular member engaged with said sleeve, said receptor tube being generally flared in the direction of flow. A signal output transmitting member is attached at the end of the receptor tube for transmitting the amplified sound to an external receiver. An orifice is provided in said sleeve intermediate the receptor tube and the second baffles for the passage of the gases which do not substantially enter the receptor tube.

12 Claims, 4 Drawing Figures

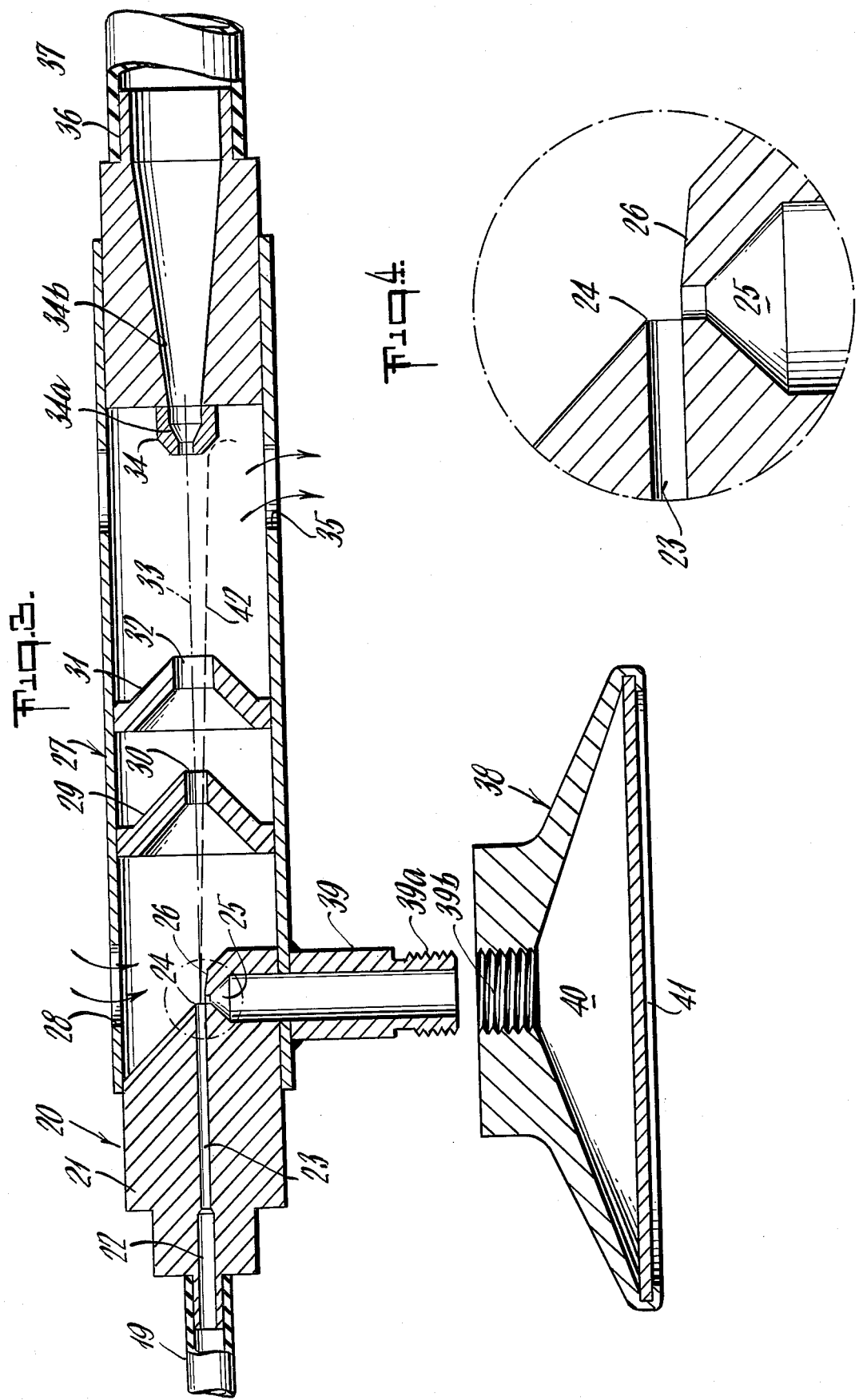

3,999,625

DEVICE FOR SIMULTANEOUS MODULATION AND AMPLIFICATION OF LOW FREQUENCY SOUNDS

BACKGROUND OF THE INVENTION

1. Field of Invention

This invention relates to a device for simultaneous frequency modulation and amplification and it is particularly related to a device which is capable of putting out an amplified reproduction of an input signal while modulating the same simultaneously. More specifically, this invention relates to a device which is sensitive to low frequencies and which is capable of amplifying low frequency sounds.

2. The Prior Art

So far as it is known, most prior art devices which have heretofore been used for amplification of low frequency sounds have been high frequency amplifiers which are not capable of amplifying low frequency sounds without simultaneously over-amplifying the surrounding high frequency sounds. A typical example of a high frequency amplifier is the well known electron microphone with a microphone pick-up, and a typical low power amplifier is the well known physician stethoscope which is commonly employed to listen to the human heart. Such stethoscopes, however, while capable of detecting low frequency sounds, have limited amplification capacity. It is frequently desirable, however, to amplify low frequency sounds without overamplifying the surrounding high frequency sounds, in order to derive valuable information, such as, for example, when listening to the human heart beat.

The device of this invention is not only capable of detecting the human heart beat, but is has the unique capability of detectng and amplifying the low frequency sounds associated therewith, such as the sound associated with the flow of blood in the human system.

SUMMARY OF THE INVENTION

This invention basically comprises a tubular member having an axial bore at the inlet end thereof for receiving gaseous or liquid flow therein. The axial bore extends a distance interiorly in said tube and tapers to a reduced axial bore therein. A generally perpendicular passageway in said tube intersects the reduced axial bore the top wall of which terminates adjacent to said intersection and the bottom wall of which extends a distance past said intersection, the said extended portion, however, being deflected at a finite angle relative to the normal axis of flow in said reduced axial bore. The tubular member is received by a sleeve, and a first baffle flared in the direction of the flow is angularly disposed relative to said sleeve to define a first passageway in said tube. A second baffle is positioned in spaced relation to the first baffle, also angularly disposed relative to the sleeve, and defines a second passageway in said tube such that the area of the second passageway is larger than the area of the first passageway. The device of this invention is also provided with a receptor tube at the outlet end of said tubular member for receiving the gaseous flow, said receptor tube being generally flared in the direction of the flow. A signal output transmitting element is provided at the outlet of said sleeve, adapted to transmit the amplified sound to an external receiver. An orifice or passageway is provided in the sleeve intermediate the receptor tube and the second baffle for the passage of the gases which do not substantially enter the receptor tube.

In one embodiment of this invention, the said generally perpendicular passageway communicates with a stethoscope head in order to amplify the sounds resulting from the heart beat and the flow of blood stream through the human body. Other and different embodiments of the invention will become more apparent from the following detailed description of the invention taken in conjunction with the accompanying drawings.

DESCRIPTION OF THE DRAWING

FIG. 3 is a side sectional view of the device of this invention with a stethoscope head detached therefrom;

FIG. 4 is an enlarged top view of the area shown by the dotted circle in FIG. 3 and illustrating the details of a specific feature of this invention.

Like numerals in the drawings designate like parts.

DETAILED DESCRIPTION OF THE INVENTION

In accordance with this invention, it has now been discovered that low frequency sounds, i.e., frequencies ranging from about 1 to about 500 cycles per second, or even somewhat higher, can be modulated and amplified simultaneously by a device which is uniquely designed for this purpose. The device of this invention can be conveniently adapted for use with other devices such as a stethoscope, blood-pressure measuring instruments, etc., although for convenience of illustration the ensuring detailed description will be directed to the application of this device in conjunction with a stethoscope.

Figure 1:
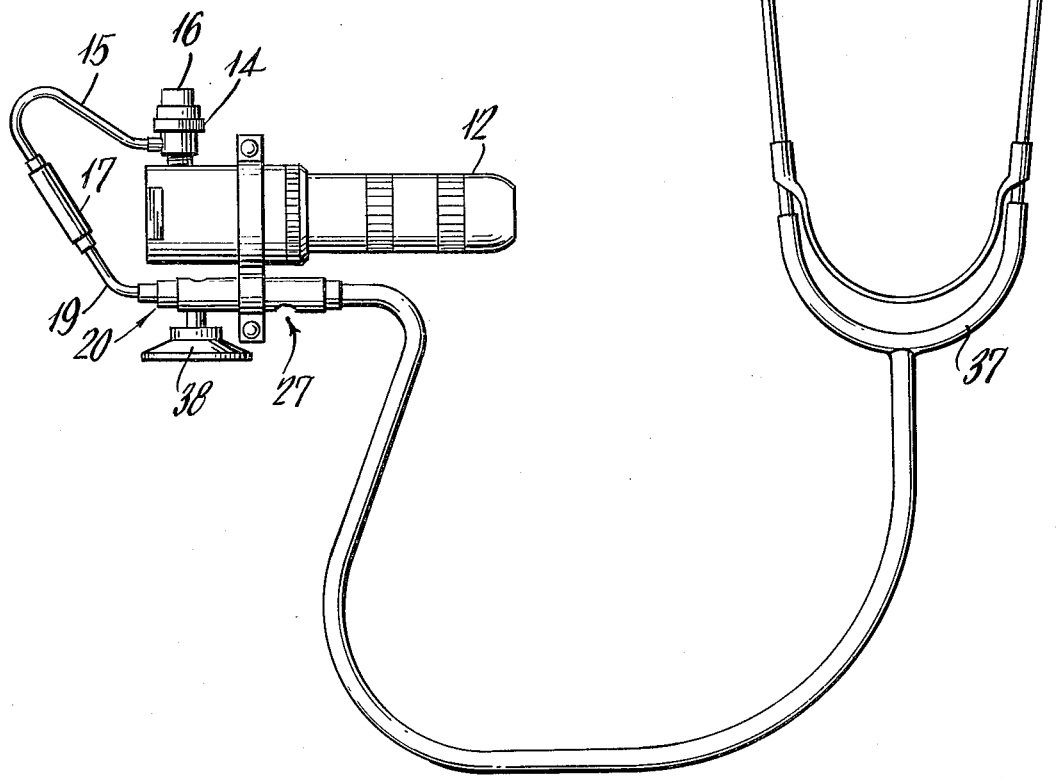
FIG. 1 is a schematic side view of one embodiment of this invention using a stethoscope in conjunction with the low frequency modulator and amplifier of this invention.
Figure 2:
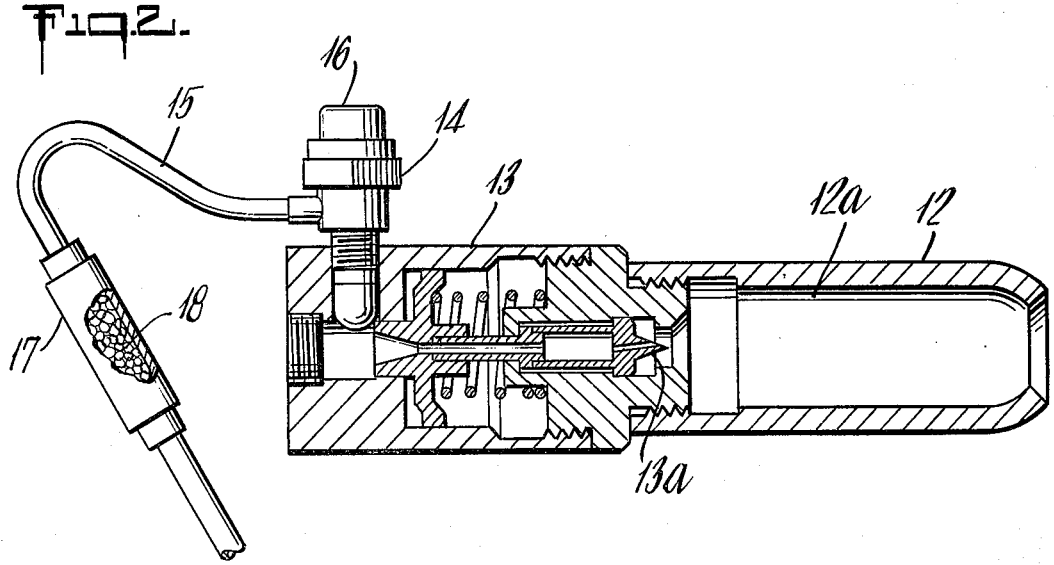
FIG. 2 is a side sectional view of the cartridge employed in the embodiment of the invention illustrated in FIG. 1.

Thus referring to the drawings, and with particular reference first to FIGS. 1 and 2, there are shown a generally cylindrical housing 12 which houses a carbon dioxide cartridge 12a (not shown). The carbon dioxide serves as the gas pressure for producing a succession of amplified gas impulses in response to an input signal. Also shown in FIGS., 1 and 2 is a second housing 13 having the usual piercing element 13a for penetrating the cap of the carbon dioxide cartridge 12a in order to release the gas contained therein. Housings 12 and 13 constitute a power pack regulator of the type readily available commercially such as, for example, the cartridge available as Model R-32 from Norgen of Littleton, Colo.

Again referring of FIGS. 1 and 2, there are shown a valve 14 activated by a push button 16 in order to discharge the carbon dioxide from the cartridge 12a through a conduit 15 and a sound absorbing chamber 17 which is filled with a sound absorbing material 18. The sound absorbing material 18 is generally an expanded plastic sponge-like material in which the individual cells communicate with one another. It has been found that the noise of rushing gas passing directly into the device shown in FIG. 3 will be so dominant as to mask the critical sounds such that they cannot be heard over the sound of the rushing gas stream. The use of a sound absorbing material will essentially suppress the noise of the rushing gas stream and will result in the flow of a gaseous stream which is free from the noise associated therewith.

From the chamber 17 the gas stream flows through the conduit 19 into a tubular member 20 which is a generally cylindrical body made of metal or plastic. Tubular member 20 comprises a body 21 which has an axial bore 22 which receives the gaseous stream from the conduit 19. The bore 22 extends a distance into the body 21 and thereafter tapers into a reduced axial bore 23. The reduced bore 23 is defined by a top wall which terminates at about the intersection 24 with a generally perpendicular passage-way 25 tapered as shown in FIG. 3. The reduced bore 23 is also defined by a bottom wall which extends a distance beyond the intersection 24 deflected as a shoulder 26 at some specified angle relative to the normal horizontal axis of tubular member 20 as shown in more detail in FIG. 4. This angle of deflection has been found to be a critical part of the device of this invention.

When used in conjunction with a stethoscope as shown in FIGS. 1 and 2 and where the diameters of the bore 22 and the reduced bore 23 are about 40 thousandths of an inch and 25 thousandths of an inch, respectively, an angle of deflection of about 6 degrees will best serve to modulate and amplify the low frequency sounds associated with the heart beat. It must be understood, however, that in other systems and where the other dimensions are changed the angle of deflection must be varied for most efficacious results.

The tubular member 20 is received by the sleeve 27 which has an opening 28. Annular cone-shaped baffle 29, flared in the direction of the gaseous flow, is preferably disposed at an angle of approximately 45° relative to the sleeve 27, and an axial passageway 30. Also shown in FIG. 3 is a baffle 31 in spaced relation to the baffle 29 and having an axial passageway 32 having a diameter slightly larger than the diameter of the axial passageway 30. The baffle 31 is also disposed at an angle of approximately 45° relative to the sleeve 27. Thus, the gaseous stream which is deflected by the shoulder 26 is deflected from its normal axial flow and passes through the baffles 29 and 31 below the normal horizontal flow axis 33.

In the sleeve 27, at the outlet end thereof, there is provided a receptor tube 34 positioned coaxially with the normal horizontal flow axis 33. An orifice 35 is provided at the bottom of the sleeve 27 to permit the escape of the gases which do not substantially enter the receptor tube 34.

The receptor tube 34 which is generally flared in the direction of the flow communicates with a fitting 36 adapted to receive a rubber stethoscope tube 37 which is connected to a normal stethoscope ear piece 43. Although the fitting 36 is received by a rubber stethoscope tube 37, in other applications of this invention, the fitting 36 may be conveniently received transducer element for transmitting the sound to a receiver.

The passageway 25 may be attached to a normal stethoscope head 38 by means of male and female plugs 39a and 39b. The stethoscope head 38 includes the usual stethoscope chamber 40 and the diaphragm 41.

The operation of the device of this invention is as follows: the carbon dioxide cartridge 12a is placed in the housing 12 and pierced by the piercing element 13a to discharge the gas into the housing 13. The push buttom 16 is then depressed to thereby open the valve 14 to permit the gas to flow successively through conduit 15, sound absorbent chamber 17, conduit 19 and through the axial bores 22 and 23. As the gaseous stream is discharged at the intersection 24, the laminar gas flow is deflected over the shoulder 26 thus causing the gas stream to be deflected from the normal axial flow 33 so that it will not substantially enter the receptor tube 34. Rather, the deflected gas stream will pursue a secondary course 42 through the baffles 29 and 31 and hence will not substantially enter the receptor tube 34.

According, when the diaphragm 41 is placed against a pulsating surface such as the chest surface in the vicinity of the heart, the pulsating surface will transmit the sound generated by the heart beat to the diaphragm 41, which will compress the air in chamber 40. The air in chamber 40 will thus be caused to flow through the passageway 25 and will intersect the gas stream flowing through the reduced axial bore at the intersection 24 thereby directing the gaseous flow from the secondary course 42 in the direction of the receptor tube 34. The gaseous stream thus flows through the receptor tube 34 and the stethoscope tube 37 into the ear piece 43.

Since the velocity of the gaseous stream issuing from the reduced bore 23 is significantly greater than the velocity of the air stream flowing through the passageway 25, the moment of force of the laminar gas flow as modulated by the gas flow from the passageway 25 will be significantly greater and hence it will produce a strong amplified sound at the ear piece 38.

In order to use the device of this invention in applications other than a stethoscope, the passageway 25 can be attached to a signal input source and the rubber stethoscope tube 37 is replaced with an appropriate signal transmitting element such as a tranducer or other similar devices used for transmitting an amplified signal to an externally located receiver element. Otherwise, the operation of the device is essentially the same as was hereinbefore described in conjunction with the stethoscope.

In the construction of the device of this invention it must be generally considered that at low pressures, the gaseous flow turbulates at greater distances from the issue point at the intersection 24 than it would at higher pressures. Thus, as the pressure of gas leaving the reduced axial bore 23 is increased, the turbulation point is moved away from the receptor tube 34 closer to the intersection 24. Therefore, the pressure of the gas leaving the intersection 24 must be controlled so that turbulation of the gas stream in pursuing the secondary course 42 does not occur before the gas reaches the approximate position of the receptor 34 in order to obtain proper amplification.

While the device of this invention has heretofore been described in terms of a stethoscope for amplifying the heart beat, it must be understood that this device may be used to perform numerous other functions such as, for example, the operation of a microphone connected to an amplification device for producing an output signal sufficient to activate valves, switches and numerous other mechanical devices. Additionally, modified embodiments of this device, can be used to monitor atmospheric pressures to warn against tornadoes and to detect and signal the passage of aircrafts. Other similar uses will normally suggest themselves where low frequency sounds are involved.

What is claimed is:
1. A device for use as a stethoscope which comprises, in combination,
  a. a fluid-containing chamber having a means for dispensing a fluid stream from said chamber, b. a tubular member for receiving the fluid stream from said chamber, said tubular member having an axial bore extending a distance interiorly of the inlet end of said tubular member, c. signal input means including a stethoscope head for providing an input signal adjacent to and generally perpendicular to the direction of the fluid stream in said tubular member, d. a deflecting surface for deflecting said fluid stream past said signal input means, and e. a receptor tube having a orifice offset from the direction of the deflected fluid stream.

2. A device as in claim 1 wherein said deflecting surface defines an angle of about 6° relative to the direction of the fluid stream.

3. A device as in claim 2 wherein said receptor tube is generally flared in the direction of the fluid stream.

4. A device as in claim 3 further including a conduit containing a fluid absorbing material, said conduit having an inlet end communicating with said chamber and an outlet end communicating with said tubular member.

5. A device as in claim 2 further including a conduit containing a fluid-absorbing material, said conduit having an inlet end communicating with said chamber and an outlet end communicating with said tubular member.

6. A device as in claim 1 wherein said receptor tube is generally flared in the direction of the fluid stream.

7. A device as in claim 6 further including a conduit containing a fluid-absorbing material, said conduit having an inlet end communicating with said chamber and an outlet end communicating with said tubular member.

8. A device as in claim 1 further including a conduit containing a fluid-absorbing material, said conduit having an inlet end communicating with said chamber and an outlet end communicating with said tubular member.

9. A device for use as a stethoscope which comprises, in combination:

a. a gas-containing chamber;

b. means for dispensing said gas from said chamber;

c. a conduit having an inlet end communicating with said chamber and an outlet end communicating with a first tubular member, said conduit containing gas-absorbing material therein;

d. an axial bore in said first tubular member for receiving the gaseous flow, said axial bore extending interiorly a distance from the inlet end of said tubular member and tapering into a reduced axial bore having a top wall and a bottom wall;

e. a generally perpendicular passageway in said first tubular member intersecting said reduced axial bore adjacent the top wall thereof and wherein said bottom wall of said reduced axial bore extends a distance past said perpendicular passageway, the said extended portion being deflected a finite angle relative to the longitudinal axis of said tubular member;

f. a stethoscope member communicating with said perpendicular passageway, said stethoscope member comprising a stethoscope head and an air-containing chamber communicating with said perpendicular passageway;

g. a second tubular member for receiving said first tubular member;

h. a first baffle flared in the direction of the gaseous flow, said baffle being angularly disposed relative to said second tubular member and defining a first passageway therein;

i. a second baffle flared in the direction of the gaseous flow, said second baffle being angularly disposed relative to said second tubular member and defining a second passageway therein, said second passageway having larger passage area than said first passageway;

j. a receptor tube at the outlet of said second tubular member, said receptor tube being generally flared in the direction of the gaseous flow and communicating with a conduit for conveying the amplified sound to an external source, and k. a passageway in said second tubular member intermediate said second baffle and said receptor tube for the passages of gases which do not substantially enter said receptor tube.

10. A device as in claim 9 wherein each of said baffles is disposed at an angle of about 45° relative to the longitudinal axis of said second tubular member.

11. A device as in claim 10 wherein said bottom wall of said reduced axial bore defines an angle of about 6° with the longitudinal axis of said first tubular member.

12. A device as in claim 9 wherein said bottom wall of said reduced axial bore defines an angle of about 6° with the longitudinal axis of said first tubular member.

* * * * *